(12) United States Patent
Kendrick et al.

(10) Patent No.: US 12,064,568 B2
(45) Date of Patent: Aug. 20, 2024

(54) CATHETER

(71) Applicant: CONVATEC LIMITED, Flintshire (GB)

(72) Inventors: Andrew Kendrick, Cheshire (GB); Julie Lambrethsen, Cheshire (GB); Oliver Walter Pfleger, Merseyside (GB); Michal Weber, Cheshire (GB)

(73) Assignee: CONVATEC LIMITED, Flintshire (GB)

( * ) Notice: Subject to any disclaimer, the term of this patent is extended or adjusted under 35 U.S.C. 154(b) by 572 days.

(21) Appl. No.: 17/238,507

(22) Filed: Apr. 23, 2021

(65) Prior Publication Data
US 2021/0346647 A1 Nov. 11, 2021

Related U.S. Application Data

(63) Continuation of application No. PCT/GB2021/050982, filed on Apr. 23, 2021.

(30) Foreign Application Priority Data

Apr. 24, 2020 (GB) .................................. 2006056

(51) Int. Cl.
*A61M 25/00* (2006.01)
(52) U.S. Cl.
CPC ...... *A61M 25/0082* (2013.01); *A61M 25/001* (2013.01); *A61M 25/0075* (2013.01);
(Continued)

(58) Field of Classification Search
CPC ............ A61M 25/0075; A61M 25/002; A61M 2025/0078; A61M 2202/0496;
(Continued)

(56) References Cited

U.S. PATENT DOCUMENTS 4,062,363 A * 12/1977 Bonner, Jr. ........ A61M 25/0111
604/517
11,376,395 B2 7/2022 Montes de Oca et al.
(Continued)

FOREIGN PATENT DOCUMENTS

EP 1852139 A1 11/2007
EP 2258435 A1 12/2010
(Continued)

OTHER PUBLICATIONS

International Search Report; European Patent Office; International Application No. PCT/GB2021/050982; Aug. 11, 2021; 4 pages.
(Continued)

*Primary Examiner* — Adam Marcetich
(74) *Attorney, Agent, or Firm* — TAFT STETTINIUS & HOLLISTER LLP; Ryan O. White; Derek B. Lavender

(57) ABSTRACT

The present invention relates to a catheter 10. The catheter 10 includes a catheter tube 12 having a tip end 13 and a distal end 14, with the distal end 14 being coupled to or forming at least part of a funnel 16 for discharging fluid from within the catheter tube 12. A sleeve 18 is provided about the catheter tube 12 which is coupled at an end thereof to the funnel 16 and extends towards the tip end 13 of the catheter tube 12. The catheter 10 additionally includes a wetting mechanism 20 which is integrally formed with the funnel 16 and includes a holding chamber 22 and a fluid outlet 26 operable to allow fluid 24 from within the holding chamber 22 to be released within the sleeve 18 for wetting an outer surface of the catheter tube 12.

23 Claims, 3 Drawing Sheets

(52) U.S. Cl.
CPC .............. *A61M 2025/0073* (2013.01); *A61M 2025/0096* (2013.01); *A61M 2210/1085* (2013.01); *A61M 2210/1089* (2013.01)

(58) Field of Classification Search
CPC ........ A61M 2210/167; A61M 25/0111; A61M 25/0017; A61M 25/0113
See application file for complete search history.

(56) References Cited

U.S. PATENT DOCUMENTS

| | | | |
|---|---|---|---|
| 11,420,016 B2 | 8/2022 | Palmer | |
| 11,420,017 B2 | 8/2022 | Hilton et al. | |
| 11,524,097 B2 | 12/2022 | Sellers et al. | |
| 11,534,573 B2 | 12/2022 | Hannon et al. | |
| 11,730,557 B2 | 8/2023 | O'Flynn et al. | |
| 11,738,169 B2 | 8/2023 | Hickmott et al. | |
| 2001/0001443 A1* | 5/2001 | Kayerod | A61M 25/002 206/364 |
| 2005/0043715 A1* | 2/2005 | Nestenborg | A61M 25/002 206/439 |
| 2006/0025753 A1* | 2/2006 | Kubalak | A61M 25/0111 604/327 |
| 2012/0110951 A1 | 5/2012 | van Groningen et al. | |
| 2016/0339205 A1* | 11/2016 | Foley | A61M 25/002 |
| 2018/0104447 A1 | 4/2018 | Madlung et al. | |
| 2018/0169377 A1* | 6/2018 | Hickmott | A61M 25/0097 |
| 2019/0201659 A1 | 7/2019 | Gustavsson et al. | |
| 2020/0155261 A1 | 5/2020 | O'Flynn et al. | |
| 2021/0196923 A1 | 7/2021 | Palmer | |
| 2021/0228836 A1 | 7/2021 | Terry | |
| 2021/0260332 A1 | 8/2021 | Panesar et al. | |
| 2021/0275727 A1 | 9/2021 | Farrell et al. | |
| 2021/0330938 A1 | 10/2021 | Kendrick et al. | |
| 2021/0346644 A1 | 11/2021 | Kendrick et al. | |
| 2021/0346647 A1 | 11/2021 | Kendrick et al. | |
| 2021/0346648 A1 | 11/2021 | Kendrick et al. | |
| 2021/0370019 A1 | 12/2021 | Erbey et al. | |
| 2022/0001139 A1 | 1/2022 | Eriksson et al. | |
| 2022/0126057 A1 | 4/2022 | Eriksson et al. | |
| 2022/0133426 A1 | 5/2022 | O'Flynn et al. | |
| 2022/0176068 A1 | 6/2022 | Pfleger et al. | |
| 2022/0176069 A1 | 6/2022 | Jenco et al. | |
| 2022/0226604 A1 | 7/2022 | Murray et al. | |
| 2022/0233808 A1 | 7/2022 | Farrell et al. | |
| 2022/0241549 A1 | 8/2022 | Murray et al. | |
| 2022/0241553 A1 | 8/2022 | Farrell et al. | |
| 2022/0288350 A1 | 9/2022 | Montes de Oca et al. | |
| 2022/0296355 A1* | 9/2022 | Göbel | A61M 25/0102 |
| 2022/0379075 A1 | 12/2022 | Hilton et al. | |
| 2022/0387673 A1 | 12/2022 | Farrell et al. | |
| 2022/0409859 A1 | 12/2022 | Sileika et al. | |
| 2023/0241288 A1 | 8/2023 | O'Mahony et al. | |

FOREIGN PATENT DOCUMENTS

| | | |
|---|---|---|
| EP | 3283136 B1 | 6/2021 |
| EP | 3854438 A1 | 7/2021 |
| EP | 3862031 A1 | 8/2021 |
| EP | 3184140 B1 | 10/2021 |
| EP | 3668555 B1 | 10/2021 |
| EP | 3727550 B1 | 10/2021 |
| EP | 3892320 A1 | 10/2021 |
| EP | 3932438 A1 | 1/2022 |
| EP | 3943140 A1 | 1/2022 |
| EP | 3952973 A1 | 2/2022 |
| EP | 3955863 A1 | 2/2022 |
| EP | 3983023 A1 | 4/2022 |
| EP | 3725355 B1 | 5/2022 |
| EP | 3991773 A1 | 5/2022 |
| EP | 3727549 B1 | 6/2022 |
| EP | 4015008 A1 | 6/2022 |
| EP | 2515988 B2 | 7/2022 |
| EP | 2968842 B1 | 7/2022 |
| EP | 3897766 B1 | 7/2022 |
| EP | 3593850 B1 | 9/2022 |
| EP | 3821934 B1 | 9/2022 |
| EP | 4051358 A1 | 9/2022 |
| EP | 4085962 A1 | 11/2022 |
| EP | 2688629 B1 | 12/2022 |
| EP | 3308823 B1 | 12/2022 |
| EP | 3793626 B1 | 12/2022 |
| EP | 2908898 B1 | 7/2023 |
| EP | 3148625 B1 | 7/2023 |
| EP | 3651844 B1 | 7/2023 |
| EP | 3119464 B2 | 8/2023 |
| EP | 4241818 A2 | 9/2023 |
| EP | 4245349 A2 | 9/2023 |
| WO | 2019123003 A1 | 6/2019 |
| WO | 2021183718 A1 | 9/2021 |
| WO | 2021240266 A1 | 12/2021 |
| WO | 2021242487 A1 | 12/2021 |
| WO | 2021242676 A1 | 12/2021 |
| WO | 2021242745 A1 | 12/2021 |
| WO | 2022002483 A1 | 1/2022 |
| WO | 2022090055 A1 | 5/2022 |
| WO | 2022108750 A1 | 5/2022 |
| WO | 2022118010 A1 | 6/2022 |
| WO | 2022118011 A1 | 6/2022 |

OTHER PUBLICATIONS

Written Opinion of the International Searching Authority; European Patent Office; International Application No. PCT/GB2021/050982; Aug. 11, 2021; 6 pages.

* cited by examiner

CATHETER

This application is a continuation of International Application No. PCT/GB2021/050982 filed Apr. 23, 2021 and claims the priority of GB Application No. 2006056.2, filed Apr. 24, 2020. The disclosures of which are hereby incorporated herein in their entirety.

TECHNICAL FIELD OF THE INVENTION

The present invention relates to a catheter (e.g. a urinary catheter) having an integral wetting mechanism for wetting a tube of the catheter, in use.

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc. remain open. Urinary catheters are designed for use for insertion into a user's bladder via the urethra to drain the bladder.

To maximise comfort and minimise the risk of trauma and/or infection, an outer surface of the catheter tube is typically lubricated using a wetting fluid prior to insertion by the user. In further developments, the catheter tube itself comprises, is integrated with or is coated with a hydrophilic component (e.g. a hydrophilic polymer) which serves to reduce friction further upon application of the wetting fluid.

Some catheters may be supplied pre-lubricated in a packaging, for instance, where the catheter is at least partially submerged within wetting fluid within the packaging. However, such arrangements suffer in that components of the catheter other than the catheter tube such as a gripper element or funnel can also become wetted. This has a detrimental effect of the experience of the user where it may become difficult to hold and direct the catheter tube as required. This is particularly problematic where the user is performing self-catheterisation. Further, having the catheter submerged may effectively reduce the shelf-life of the catheter due to long-term exposure of components of the catheter to moisture.

It is therefore seen advantageous to provide a catheter which may be lubricated at or immediately prior to the point of use.

In an attempt to address this, some catheters are provided in packaging which includes a rupturable container or sachet within the packaging which a user may burst to release the wetting fluid. Typically, this involves the user squeezing the packaging to cause the container/sachet to break. However, such arrangements experience similar problems to those discussed above where the wetting fluid is allowed to come into contact with other components of the catheter.

As an extension to such solutions, some prior art catheters replace the container with a wetting device initially coupled at a distal end of the catheter tube which may be slid along the catheter tube by the user whilst releasing fluid contained within the device to wet the catheter tube. However, such solutions suffer similar drawbacks in that the wetting fluid may typically be released into the packaging. Furthermore, such solutions rely on a series of relatively complex actions to be performed the user in order to adequately wet the catheter tube which, if not done correctly, may result in injury and/or infection. These solutions may also be relatively complex to manufacture given the number of moving components.

It would therefore be advantageous to provide a catheter which includes a means to supply a wetting fluid solely to the catheter tube to improve user experience. It would also be advantageous to provide a catheter which includes a means to supply a wetting fluid which is of lower complexity in terms of use and/or manufacture when compared with prior art devices.

It is an aim of an embodiment or embodiments of the invention to overcome or at least partially mitigate one or more problems with the prior art.

SUMMARY OF THE INVENTION

According to an aspect of the invention there is provided a catheter, comprising: a catheter tube having a distal end coupled to or forming at least part of a funnel for discharging fluid from within the catheter tube; a sleeve provided about the catheter tube, coupled at an end thereof to the funnel; and a wetting mechanism integrally formed with the funnel, the wetting mechanism comprising: a holding chamber having a volume of fluid contained therein; and a fluid outlet operable to allow fluid from within the holding chamber to be released within the sleeve for wetting an outer surface of the catheter tube.

According to a further aspect of the invention there is provided a catheter, comprising: a catheter tube having a tip end and a distal end, the distal end coupled to or forming at least part of a funnel for discharging fluid from within the catheter tube; a sleeve provided about the catheter tube, coupled at an end thereof to the funnel and extending towards the tip end of the catheter tube; and a wetting mechanism integrally formed with the funnel, the wetting mechanism comprising: a holding chamber having a volume of fluid contained therein; and a fluid outlet operable to allow fluid from within the holding chamber to be released within the sleeve for wetting an outer surface of the catheter tube.

Advantageously, the catheter of the present invention provides a means—i.e. the integrated wetting mechanism—for wetting an outer surface of the catheter tube directly and at the point of use. Firstly, this has benefits in terms of shelf-life of the product as the wetting fluid and catheter tube may be kept separate from one another up until the point of use. Furthermore, releasing the wetting fluid into the sleeve lubricates the catheter tube without exposing further components of the catheter (e.g. the funnel itself, gripper or outer surface of the sleeve) to the wetting fluid. Again, this overcomes user experience issues associated with catheters which are submerged to lubricate the catheter tube, or where fluid may be released into the packaging, in general. Having the wetting mechanism integrally formed with the funnel may additionally provide benefits in terms of manufacturing cost and complexity, and may in some instances reduce the number of separate components of the catheter and packaging, realising benefits in terms of disposal of the catheter after use.

The wetting mechanism and funnel may be integrally formed as a single component. For example, the wetting mechanism and funnel may be formed of a single moulded component. Alternatively, the wetting mechanism and funnel may be separate components, but which are permanently secured or bonded to one another to form a single, integrally formed component of the catheter.

The funnel may comprise one or more walls. The one or more walls may comprise an internal wall and/or an external wall. The one or more walls of the funnel may at least partially define the holding chamber. For example, the holding chamber may be defined, at least in part, by one or more internal walls of the funnel. In presently preferred embodiments the holding chamber is at least partially defined by an internal wall and an external wall of the funnel.

In some embodiments one or more walls of the funnel may define, at least in part, an outlet for fluid within the catheter tube. For example, one or more walls of the funnel, in particular one or more internal walls, may define a bore through the funnel through which fluid within the catheter tube may be discharged, in use. The funnel may be configured such that the distal end of the catheter tube may be located at least partially within or through said bore to retain the catheter tube within the funnel. The distal end of the catheter tube may be fixed in the bore of the funnel, e.g. the distal end of the catheter tube may be bonded or otherwise secured, or moulded as part of the bore through the funnel.

The funnel may comprise an internal wall which separates the holding chamber and the outlet of the catheter tube.

In embodiments the funnel may be formed at least partly of a rigid material. For example, one or more internal walls of the funnel may be formed of a rigid material. In presently preferred embodiments the funnel may be at least partly formed of a flexible material. The funnel may be at least partly formed of a compressible material.

In embodiments, the funnel comprises a wall, preferably an external wall, which includes a flexible and/or compressible portion. The flexible and/or compressing portion may be formed of a resilient material, which may be configured to deform from a first configuration upon application of a force by a user (e.g. a user squeezing the funnel). The flexible and/or compressible portion may define an interaction region of the funnel. The interaction region may be configured to compress, bend and/or flex upon application of a force by a user, e.g. upon a user squeezing the funnel. The interaction region may be configured such that, in use, compressing, bending and/or flexing of the interaction region causes release of fluid from the holding chamber through the fluid outlet.

The catheter tube may have a length of up to (and possibly upwards) of 35 cm. The catheter tube may be up to or at least 20 cm, up to or at least 25 cm, up to or at least 30 cm, up to or at least 35 cm, or up to or at least 40 cm, in length, for example. In embodiments, the catheter tube may be more than 40 cm in length. In preferred embodiments, the catheter tube is between 25-35 cm, in length.

In embodiments, the fluid outlet comprises a valve arrangement. The valve arrangement may be provided as part of the funnel, for example, forming a closable aperture within a wall of the funnel. The valve arrangement may be configured to open to allow fluid to flow therethrough upon compressing, bending and/or flexing of the funnel. The valve arrangement may comprise one or more valves.

In some embodiments the fluid outlet comprises a frangible portion of the funnel, e.g. a frangible portion within a wall of the funnel. The frangible portion may be configured open in response to compressing, bending and/or flexing the funnel, for example, upon application of a force by a user on one or more walls of the funnel. Opening the frangible portion may comprise rupturing, splitting or otherwise breaking the frangible portion to form an aperture in the holding chamber defining the fluid outlet.

When used herein and throughout the specification the terms "opening" or "to open" when referring to the fluid outlet may be taken to mean moving to a configuration where fluid contained within the holding chamber is able to flow from the holding chamber, through the outlet.

In some embodiments the fluid may be contained within a container within the holding chamber. The container may comprise a sachet, blister pack or capsule, for example, positioned within the holding chamber and holding fluid therein. The wetting mechanism may be configured such that the container may be ruptured, split or otherwise broken upon compressing, bending and/or flexing the funnel, for example. In use, rupturing, splitting or otherwise breaking the container may cause release of the contained fluid from the container—e.g. to cause the released fluid to flow through the fluid outlet and into the sleeve of the catheter.

In embodiments wherein the fluid is contained within a container within the holding chamber, the fluid outlet may comprise an aperture within the holding chamber allowing fluid to flow freely therethrough upon release from the container—e.g. in the manner described herein.

One particularly preferred embodiment provides a catheter, comprising: a catheter tube having a tip end and a distal end, the distal end coupled to or forming at least part of a funnel for discharging fluid from within the catheter tube; a sleeve provided about the catheter tube, coupled at an end thereof to the funnel and extending towards the tip end of the catheter tube; and a wetting mechanism integrally formed with the funnel, the wetting mechanism comprising: a holding chamber having a volume of fluid contained within a container within the holding chamber; and a fluid outlet operable to allow fluid from within the holding chamber to be released within the sleeve for wetting an outer surface of the catheter tube; wherein the fluid outlet comprises an aperture within the holding chamber allowing fluid to flow freely therethrough upon release from the container.

The sleeve may preferably comprise a flexible sleeve. In embodiments, the sleeve may be formed of film of plastics material.

In embodiments the funnel may comprise a circular profile. The holding chamber may be positioned about (e.g. circumferentially about) an outlet of the catheter tube. In some embodiments the funnel may comprise a polygonal profile. The funnel may comprise a substantially triangular profile. In such embodiments, an outlet of the catheter tube may be positioned at a first apex, with the holding chamber extending at least partially between the other apices. Advantageously, having the holding chamber extending between the other apices may provide a surface (i.e. the exterior surface of the funnel adjacent to the holding chamber) extending between the two apices upon which a user may act to cause release of the wetting fluid through the fluid outlet.

Another particularly preferred embodiment provides a catheter, comprising: a catheter tube having a tip end and a distal end, the distal end coupled to or forming at least part of a funnel for discharging fluid from within the catheter tube; a sleeve provided about the catheter tube, coupled at an end thereof to the funnel and extending towards the tip end of the catheter tube; and a wetting mechanism integrally formed with the funnel, the wetting mechanism comprising: a holding chamber having a volume of fluid contained therein; and a fluid outlet operable to allow fluid from within the holding chamber to be released within the sleeve for wetting an outer surface of the catheter tube; wherein the funnel comprises a substantially triangular profile.

Another particularly preferred embodiment provides a catheter, comprising: a catheter tube having a tip end and a distal end, the distal end coupled to or forming at least part of a funnel for discharging fluid from within the catheter tube; a sleeve provided about the catheter tube, coupled at an end thereof to the funnel and extending towards the tip end of the catheter tube; and a wetting mechanism integrally formed with the funnel, the wetting mechanism comprising: a holding chamber having a volume of fluid contained therein; and a fluid outlet operable to allow fluid from within the holding chamber to be released within the sleeve for wetting an outer surface of the catheter tube; wherein the funnel comprises a substantially triangular profile and an outlet of the catheter tube is positioned at a first apex, with the holding chamber extending at least partially between the other apices.

The holding chamber may be configured to hold up to 0.25 ml, or up to 0.5 ml, or up to 0.75 ml, or up to 1.0 ml, or up to 1.5 ml, or up to 2.0 ml, or up to 2.5 ml, or up to 3.0 ml, or up to 4.0 ml, or up to 5.0 ml of wetting fluid, for example.

In embodiments the wetting mechanism may comprise a fluid release control component for controlling release of the fluid from the holding chamber. The fluid release control component may be moveable between first and second positions. The fluid release control component may be moveable between first and second positions to control the release of fluid from within the holding chamber. For example, the first position may correspond to a position wherein the fluid release control component prevents release of fluid from within the holding chamber. In such embodiments, the second position may correspond to a position wherein the fluid release control component allows for the release of fluid from within the holding chamber. For example, in moving from the first position to the second position may cause the fluid outlet of the wetting mechanism.

The fluid release control component may be linearly moveable. The fluid release control component may be rotatable.

In some embodiments the fluid release control component comprises a plug. The plug may be configured to be at least partly withdrawn from the wetting mechanism to cause release of the fluid from the holding chamber. The plug may be configured to be at least partly withdrawn from the first position to the second position. For example, in such embodiments, the plug may be at least partly received within or otherwise coupled to the remainder of the wetting mechanism in the second position. In some embodiments the plug may be configured such that it must be fully withdrawn from the wetting mechanism to cause release of the fluid from the holding chamber. In such embodiments, the second position of the plug may correspond to a position in which the plug is completely removed and separate from the remainder of the wetting mechanism.

The catheter may comprise a gripper element. The gripper element may be coupled to the sleeve of the catheter. In presently preferred embodiments the funnel is coupled to the sleeve at a first end of the sleeve, with the gripper element coupled at an opposing end of the sleeve. The gripper element may, at least initially, be positioned at or proximal to the tip end of the catheter. The catheter may be configured such that the catheter tube may be moved through the gripper element to expose the catheter tube (e.g. for use).

In embodiments, the gripper element may comprise a fluid flow control component to control flow of fluid (e.g. the wetting fluid) through the gripper element. In some embodiments the fluid flow control component may be configured to prevent or substantially reduce the flow of fluid through the gripper element. Advantageously, the fluid flow control component may prevent excess wetting fluid being discharged from the catheter, and specifically from within the sleeve about the catheter tube, thereby preventing excess fluid from coming into contact with other components of the catheter (e.g. an outer surface of the funnel or gripper element). This may provide benefits in terms of usability of the catheter for the end user.

The fluid flow control component may comprise an absorbent material such as a foam, sponge or wicking material, for example, able to absorb the wetting fluid, in use.

The fluid flow control component may be configured to act as a wetting applicator able to release fluid contained therein upon movement of the catheter tube against the fluid flow control component—e.g. when moving the catheter tube through the gripper element, in use. Advantageously, the fluid flow control component may provide two separate functions by both preventing leakage of wetting fluid from the sleeve, and acting to control the distribution of wetting fluid on the exterior of the catheter tube.

The catheter may comprise a urinary catheter. The catheter may comprise a male urinary catheter or a female urinary catheter. The catheter may comprise a single-use catheter. The catheter may comprise an intermittent urinary catheter.

According to an aspect of the invention there is provided a sealed packaged catheter according to the preceding aspect of the invention.

According to an aspect of the invention there is provided a method for wetting a tube of a catheter of any aspect described herein, the method comprising: operating the wetting mechanism to release fluid from the holding chamber within the sleeve for wetting an outer surface of the catheter tube.

The method may comprise compressing, bending and/or flexing the funnel to operate the wetting mechanism. The method may comprise compressing, bending and/or flexing the funnel to open (e.g. rupture, split or otherwise break) a frangible portion in a wall of the funnel to form an aperture in the holding chamber defining the fluid outlet.

In embodiments, the fluid may be contained within a container (e.g. a sachet, blister pack or capsule) within the holding chamber and the method may comprise compressing, bending and/or flexing the funnel in order to open (e.g. rupture, split or otherwise break) the container, for example, to cause release of the contained fluid from the container—e.g. to cause the released fluid to flow through the fluid outlet and into the sleeve of the catheter.

The method may comprise operating a fluid release control component of the catheter to cause release of the fluid. Operating a fluid release control component may comprise moving the fluid release control component from a first configuration wherein it prevents release of the fluid from the holding chamber to a second configuration wherein it allows release of the fluid from the holding chamber.

DETAILED DESCRIPTION OF THE INVENTION

In order that the invention may be more clearly understood one or more embodiments thereof will now be described, by way of example only, with reference to the accompanying drawings, of which:

FIG. 1 is a schematic view of a first embodiment of a catheter in accordance with the invention;

FIG. 2 corresponds to section 'A' of FIG. 1, and shows a cross-sectional view of a funnel forming part of the catheter of FIG. 1;

Figure 1:
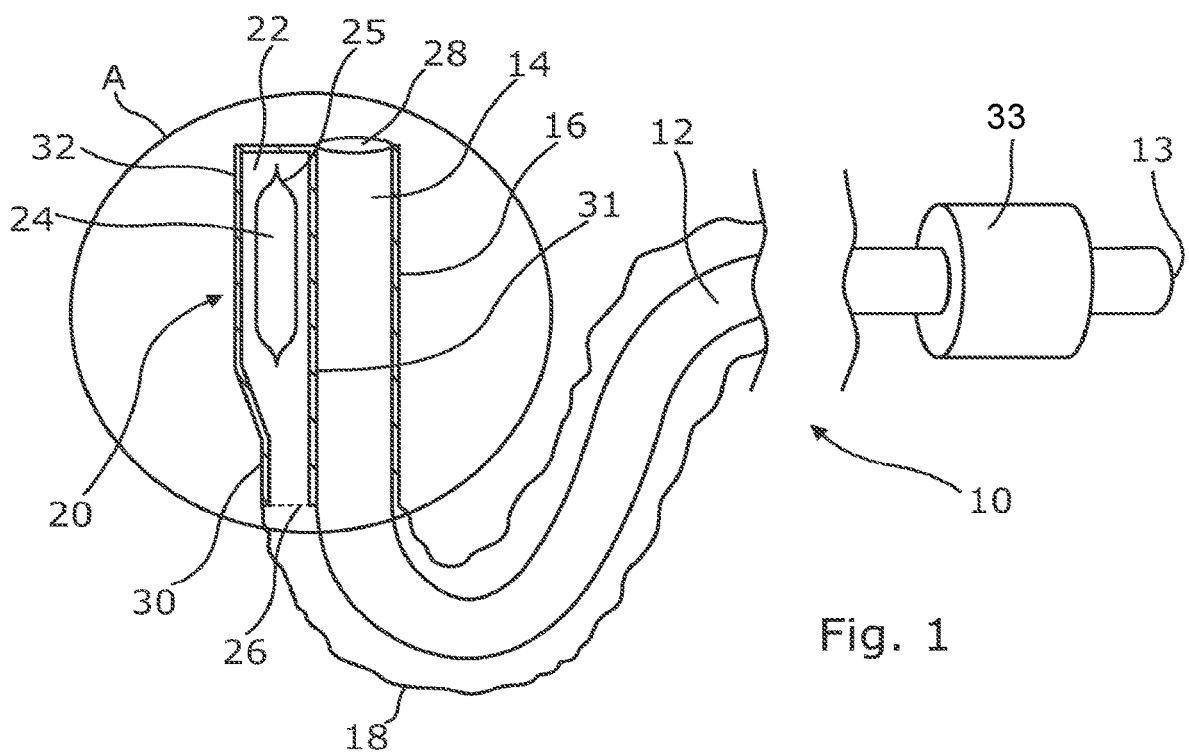
Figure 2:
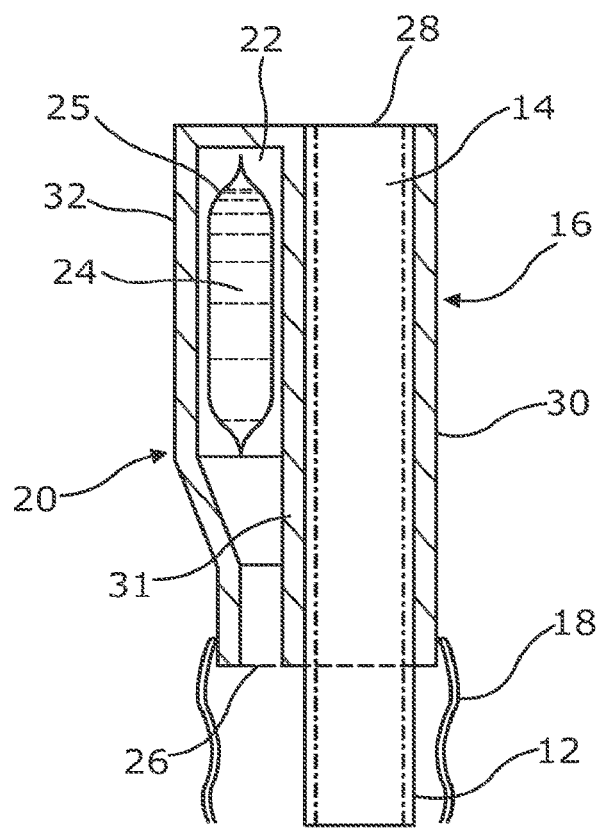

In general, the present invention relates to a catheter 10, 10' which includes a wetting mechanism 20, 20' for wetting an outer surface of a catheter tube 12, 12'.

FIGS. 1-4B illustrate a first embodiment of a catheter 10 of the invention. The catheter 10 comprises a catheter tube 12, funnel 16 and gripper element 33. A sleeve 18 is provided between the funnel 16 and gripper element 33, enclosing the catheter tube 12 between the funnel 16 and the gripper element 33. In the illustrated embodiment, the sleeve is formed of a film of flexible material and is coupled at a first end to the funnel 16 and at a second end to the gripper element 33. In this way, the sleeve 18 defines an internal volume about the catheter tube 12 into which fluid may be introduced to wet the outer surface of the catheter tube 12.

As will be appreciated, the catheter tube 12 may be moved through the gripper element 33, in use, to expose the catheter tube 12 for use by the user. Further, whilst the catheter 10 is shown in FIG. 1 with the tip of the catheter tube 12 exposed it will be appreciated that the catheter tube 12 may, at least initially, be provided within the volume defined by the sleeve 18, or at least within the gripper element 33, to enable the tip of the catheter tube 12 to be wetted using the wetting mechanism 20 before being subsequently pushed through the gripper element 33 to expose the catheter tube 12 for use.

The catheter tube 12 has a tip end 13 and a distal end 14. The tip end 13 includes a tip for insertion of the catheter tube 12 into a canal, vessel, passageway, body cavity, etc. for removal of fluid therefrom. Here, the catheter 10 comprises a urinary catheter 10 with the tip configured for insertion into a patient's bladder. The tip end 13 of the catheter tube includes apertures (not shown) therein for allowing for fluid to enter the interior of the catheter tube 12. The distal end 14 of the catheter tube 12 is integrally formed within the funnel 16. Specifically, the distal end 14 of the catheter tube 12 is fixed within the funnel 16 (e.g. through suitable bonding, adhesive, or perhaps moulded together, or the like) and includes an outlet 28 which serves as an outlet for discharging fluid from within the catheter tube 12.

A wetting mechanism 20 is provided which is integrally formed with the funnel 16. The wetting mechanism 20 is provided for supplying a wetting fluid 24 onto an exterior surface of the catheter tube 12. In the illustrated embodiment, the wetting mechanism 20 comprises a holding chamber 22 which includes a volume of fluid 24 contained therein. Specifically, the fluid is contained within a container in the form of a sachet 25. As will be described in detail herein, fluid 24 may be released from said sachet 25, in use, for wetting the exterior surface of the catheter tube 12. To allow for this, the wetting mechanism 20 includes a fluid outlet 26 operable to allow fluid from within the holding chamber 22 to be released within the sleeve 18.

As shown, the wetting mechanism 20 and the outlet 28 are provided in a side-by-side arrangement within the funnel 16. Specifically, the funnel comprises a series of walls including an external wall 30 and an internal wall 31 which define the holding chamber 22 of the wetting mechanism 20 on a first side of the internal wall 31. The holding chamber 22 is enclosed on three sides by the external and internal walls 30, 31, with an opening provided on a fourth side (a lower side in the orientation shown in the drawings, opposite to the outlet 28 for discharging fluid from the catheter tube 12, which is the upper side in the orientation shown in the drawings) acting as the fluid outlet 26 of the wetting mechanism 20. The catheter tube 12 is positioned on the opposing side of the internal wall 31 to the holding chamber 20 within a bore through the funnel 16 defined by the external and internal walls 30, 31.

Figure 4A:
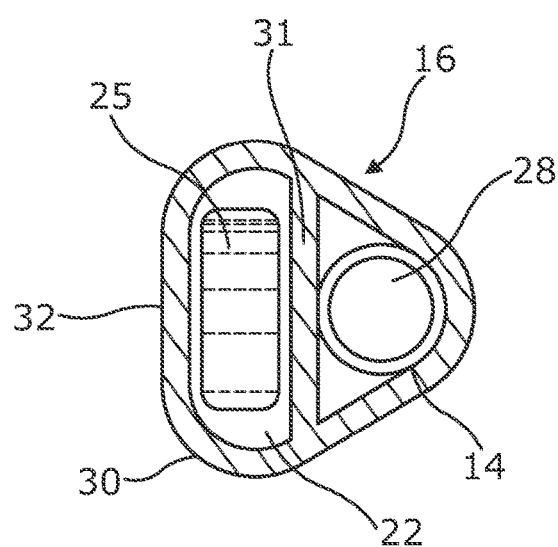
FIGS. 4A and 4B are top cross-sectional views of the funnel of FIG. 2, again illustrating the operational use of the catheter of FIG. 1.
Figure 4B:
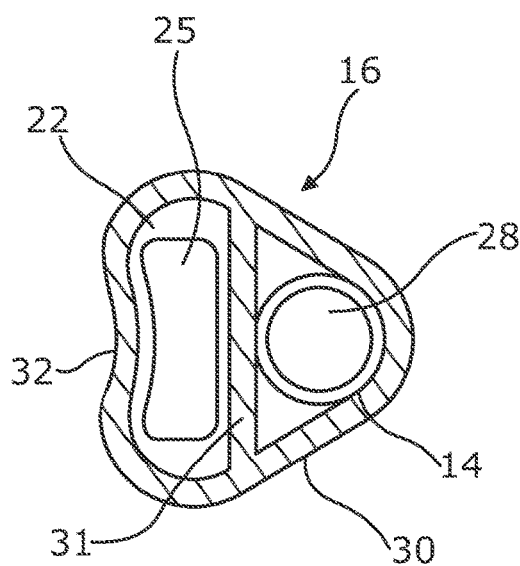

As shown, the funnel 16 comprises a substantially triangular profile, with the outlet 28 of the catheter tube 12 positioned at a first apex and the holding chamber 22 extending between the other apices of the funnel (see FIGS. 4A and 4B). In this way, the walls 30, 31 of the funnel 16 define the holding chamber 22 with an exterior surface of the funnel 16 adjacent to the holding chamber 22. Here, the exterior surface defines an interaction region 32 upon which a user may act to cause release of the wetting fluid 24 through the fluid outlet 26 as described herein. The interaction region 32 is formed of a flexible material which may depress upon application of a force by a user—i.e. upon a user squeezing the funnel 16. The remaining walls of the funnel 16 are formed of a rigid material which, along with the catheter tube 12, provide structural support for the funnel 16, and ensures the funnel 16 as a whole does not collapse upon squeezing of the funnel 16 by the user.

FIGS. 3A-4B illustrate the operational use of catheter 10, and specifically how wetting mechanism 20 may be used to wet an outer surface of the catheter tube 12.

Figure 3A:
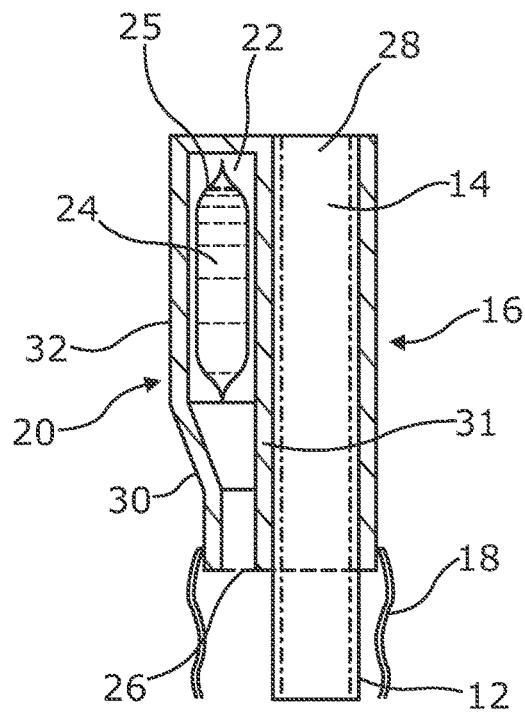
FIGS. 3A and 3B are side cross-sectional views of the funnel of FIG. 2, illustrating the operational use of the catheter of FIG. 1.
Figure 3B:
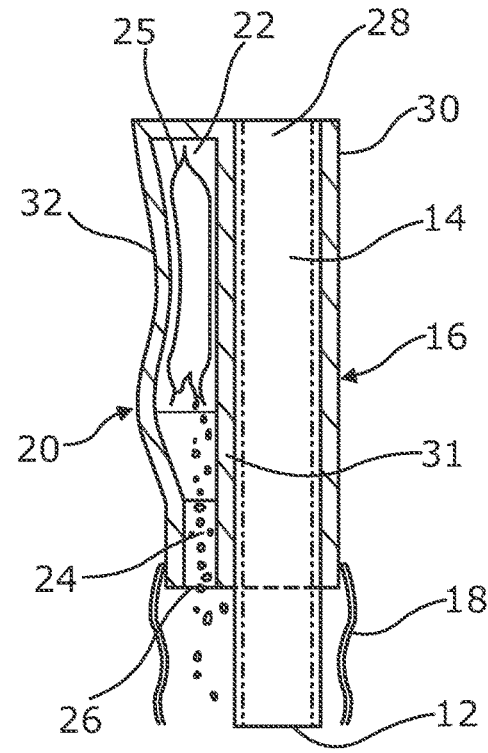

FIGS. 3A and 4A illustrate the catheter 10 prior to activation of the wetting mechanism 20, specifically with sachet 25 intact and the wetting fluid 24 contained therein. In order to activate the wetting mechanism 20, a user must squeeze the funnel 16 to provide an external force on the interaction region 32. This in turn causes the flexible interaction region 32 to depress and contact the sachet 25 within the holding chamber 22 (as shown in FIGS. 3B and 4B). The sachet 25 is in turn compressed within the holding chamber 22 causing it to rupture allowing wetting fluid 24 to escape and be released from within the holding chamber 22 through fluid outlet 26. As described herein, the fluid outlet 26 comprises an opening within the funnel 16 and therefore fluid released from the sachet 25 is able to flow through the fluid outlet 26 freely. As shown, the fluid 24 is released into the volume defined by the sleeve 18 about the exterior surface of the catheter tube 12 and is contained therein for wetting the catheter tube 12 for use.

Figure 5B:
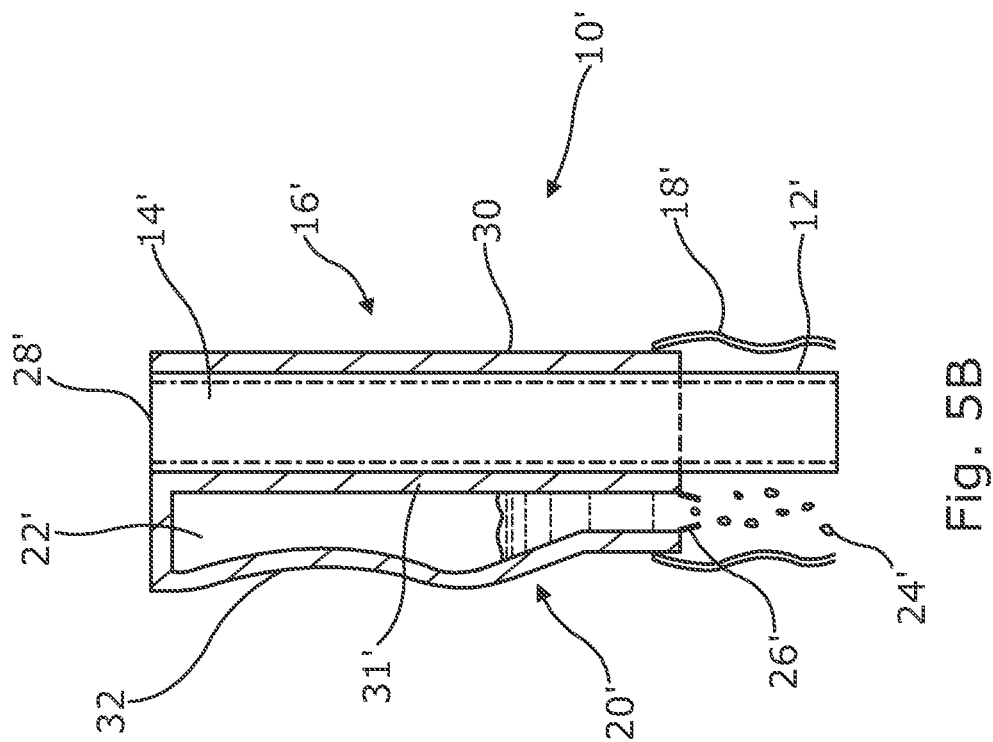
FIGS. 5A and 5B are side-cross sectional views of a funnel forming part of a second embodiment of a catheter in accordance with the invention.
Figure 5A:
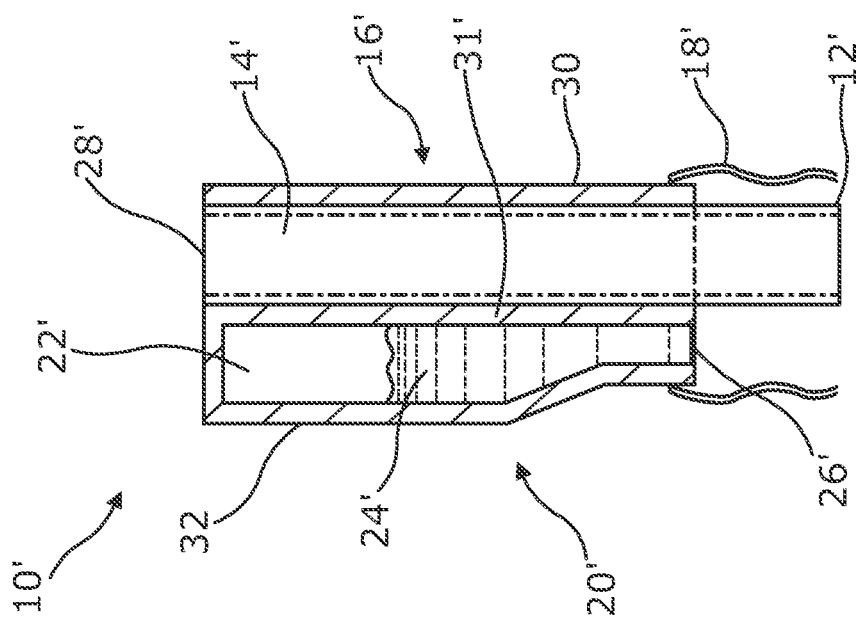

FIGS. 5A and 5B illustrate a second embodiment of a catheter 10` according to the invention. Unless otherwise described herein, the catheter 10` is configured in substantially the same way as catheter 10 shown in the preceding Figures. Like reference numerals have been used to identify equivalent components of the catheters 10, 10`.

Catheter 10' differs in the configuration of the wetting mechanism 20`. Specifically, wetting mechanism 20` has the wetting fluid 24` contained within the holding chamber 22` itself rather than within a separate container. In addition, the fluid outlet of the wetting mechanism 20' takes the form of a valve 26` which may open and close in use to allow or restrict flow of the wetting fluid 24` from the holding chamber 24`.

In use, the wetting mechanism 20` is provided in the configuration shown in FIG. 5A, with the valve 26` closed and the wetting fluid 24` held within the holding chamber 22`. In order to activate the wetting mechanism 20`, a user must squeeze the funnel 16` to provide an external force on the interaction region 32`. This in turn causes the flexible interaction region 32` to depress, reducing the volume of the holding chamber 22` (as shown in FIG. 5B). This reduction in volume (and the associated increase in pressure)

causes the valve 26` to open allowing the wetting fluid 24` to flow therethrough. As with catheter 10, the fluid 24` is released into the volume defined by the sleeve 18` about the exterior surface of the catheter tube 12` and is contained therein for wetting the catheter tube 12` for use. Upon removal of the external force applied to the interaction region 32`, the flexible interaction region 32` moves back to the configuration shown in FIG. 5A, thereby increasing the volume of the holding chamber 22` and in turn closing the valve 26'.

In a variant of catheter 10`, the valve 26` may be replaced with a frangible portion of the funnel 16` which may rupture upon an increase in pressure within the holding chamber 22` (i.e. upon squeezing of the funnel 16` by the user). Rupturing of the frangible portion results in a permanent opening within the holding chamber 22` allowing the wetting fluid 24` to flow freely into the sleeve 18`. Advantageously, in this scenario a user may not have to maintain the applied force to release all of the wetting fluid 24`, but instead simply squeezes the funnel 16` once to rupture the frangible portion.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Each of the documents referred to above is incorporated herein by reference. Except in Examples, or where otherwise explicitly indicated, all numerical quantities in this description specifying amounts of materials, device dimension, and the like, are to be understood as modified by the word "about."

Unless otherwise indicated, each chemical or composition referred to herein should be interpreted as being a commercial grade material which may contain the isomers, by-products, derivatives, and other such materials which are normally understood to be present in the commercial grade.

The one or more embodiments are described above by way of example only.

Many variations are possible without departing from the scope of protection afforded by the appended claims.

The invention claimed is:

1. A catheter, comprising:
 a catheter tube having a tip end and a distal end, the distal end coupled to or forming at least part of a funnel for discharging fluid from within the catheter tube;
 a sleeve provided about the catheter tube, coupled at an end thereof to the funnel and extending towards the tip end of the catheter tube; and
 a wetting mechanism integrally formed with the funnel, the wetting mechanism comprising: a holding chamber having a volume of fluid contained therein; and a fluid outlet operable to allow fluid from within the holding chamber to be released within the sleeve for wetting an outer surface of the catheter tube.

2. A catheter as claimed in claim 1, wherein the funnel comprises one or more walls which at least partially define the holding chamber.

3. A catheter as claimed in claim 1, wherein one or more walls of the funnel define, at least in part, an outlet for fluid within the catheter tube.

4. A catheter as claimed in claim 1, wherein the funnel is at least partly formed of a flexible material.

5. A catheter as claimed in claim 4, wherein the funnel is at least partly formed of a compressible material.

6. A catheter as claimed in claim 4, wherein the funnel comprises a wall which includes a flexible and/or compressible portion defining an interaction region of the funnel, wherein the interaction region is configured to compress, bend and/or flex upon application of a force by a user.

7. A catheter as claimed in claim 6, wherein the interaction region is configured such that, in use, compressing, bending and/or flexing of the interaction region causes release of fluid from the holding chamber through the fluid outlet.

8. A catheter as claimed in claim 1, wherein the fluid outlet comprises a valve arrangement.

9. A catheter as claimed in claim 8, wherein the valve arrangement is provided as part of the funnel and forms a closable aperture within a wall of the funnel.

10. A catheter as claimed in claim 8, wherein the valve arrangement is configured to open to allow fluid to flow therethrough upon compressing, bending and/or flexing of the funnel.

11. A catheter as claimed in claim 1, wherein the fluid outlet comprises a frangible portion of the funnel.

12. A catheter as claimed in claim 11, wherein the frangible portion is configured open, in use, in response to compressing, bending and/or flexing the funnel.

13. A catheter as claimed in claim 1, wherein the fluid is contained within a container within the holding chamber.

14. A catheter as claimed in claim 13, wherein the container comprises a sachet, blister pack or capsule positioned within the holding chamber and holding fluid therein.

15. A catheter as claimed in claim 13, wherein the wetting mechanism is configured such that the container is ruptured, split or otherwise broken upon compressing, bending and/or flexing the funnel.

16. A catheter as claimed in claim 15, wherein rupturing, splitting or otherwise breaking the container causes release of the contained fluid from the container, thereby causing the released fluid to flow through the fluid outlet and into the sleeve of the catheter.

17. A catheter as claimed in claim 13, wherein the fluid outlet comprises an aperture within the holding chamber allowing fluid to flow freely therethrough upon release from the container.

18. A catheter as claimed in claim 1, wherein the funnel comprises a substantially triangular profile comprising three apices.

19. A catheter as claimed in claim 18, wherein an outlet of the catheter tube is positioned at a first apex of the triangular profile, with the holding chamber extending at least partially between the other apices.

20. A catheter as claimed in claim 1, wherein the wetting mechanism comprises a fluid release control component for controlling release of the fluid from the holding chamber.

21. A catheter as claimed in claim 20, wherein the fluid release control component is moveable between a first position corresponding to a position wherein the fluid release control component prevents release of fluid from within the holding chamber, and a second position corresponding to a position wherein the fluid release control component allows for the release of fluid from within the holding chamber.

22. A catheter as claimed in claim 20, wherein the fluid release control component comprises a plug configured to be at least partly withdrawn from the wetting mechanism to cause release of the fluid from the holding chamber.

23. A catheter as claimed in claim 1, comprising a gripper element, wherein the funnel is coupled to the sleeve at a first end of the sleeve, with the gripper element coupled at an opposing end of the sleeve.

\* \* \* \* \*